(12) United States Patent
Watkins et al.

(10) Patent No.: US 11,285,045 B2
(45) Date of Patent: Mar. 29, 2022

(54) HELMET ASSEMBLIES WITH FLIP-TYPE WELDING VISORS

(71) Applicant: A.C.E. INTERNATIONAL COMPANY, INC., Taunton, MA (US)

(72) Inventors: James Watkins, East Taunton, MA (US); Ed Martin, Plymouth, MA (US)

(73) Assignee: A.C.E. INTERNATIONAL COMPANY, INC., Taunton, MA (US)

( * ) Notice: Subject to any disclaimer, the term of this patent is extended or adjusted under 35 U.S.C. 154(b) by 242 days.

(21) Appl. No.: 16/636,100

(22) PCT Filed: Aug. 14, 2017

(86) PCT No.: PCT/US2017/046692
§ 371 (c)(1),
(2) Date: Feb. 3, 2020

(87) PCT Pub. No.: WO2019/035801
PCT Pub. Date: Feb. 21, 2019

(65) Prior Publication Data
US 2021/0161716 A1 Jun. 3, 2021

(51) Int. Cl.
*A61F 9/06* (2006.01)
*A42B 3/22* (2006.01)

(52) U.S. Cl.
CPC .............. *A61F 9/064* (2013.01); *A42B 3/225* (2013.01)

(58) Field of Classification Search
CPC ........................................................ A61F 9/064
USPC ............................................................. 2/8.5
See application file for complete search history.

(56) References Cited

U.S. PATENT DOCUMENTS

| | | |
|---|---|---|
| 3,866,244 A | 2/1975 | Ruck |
| 5,380,032 A | 1/1995 | Challande et al. |
| 2017/0112226 A1 | 4/2017 | Watkins et al. |
| 2021/0161716 A1* | 6/2021 | Watkins ................. A42B 3/225 |

* cited by examiner

*Primary Examiner* — Gloria M Hale
(74) *Attorney, Agent, or Firm* — McClure, Qualey & Rodack, LLP

(57) ABSTRACT

Improvements to helmet assemblies with flip-type welding visors are provided. In one embodiment, a return mechanism applies a predetermined force to a wireform spring. The return mechanism applies a force between a welding visor and a grinding shell, while concurrently reducing rotational forces needed to flip up the welding visor from the grinding shell. In another embodiment, a combination of an adjustable spring and a slide stop provides an adjustable stopping position for the wireform spring. The adjustable stopping position permits adjustable balancing of the forces that are applied to the wireform spring.

12 Claims, 14 Drawing Sheets

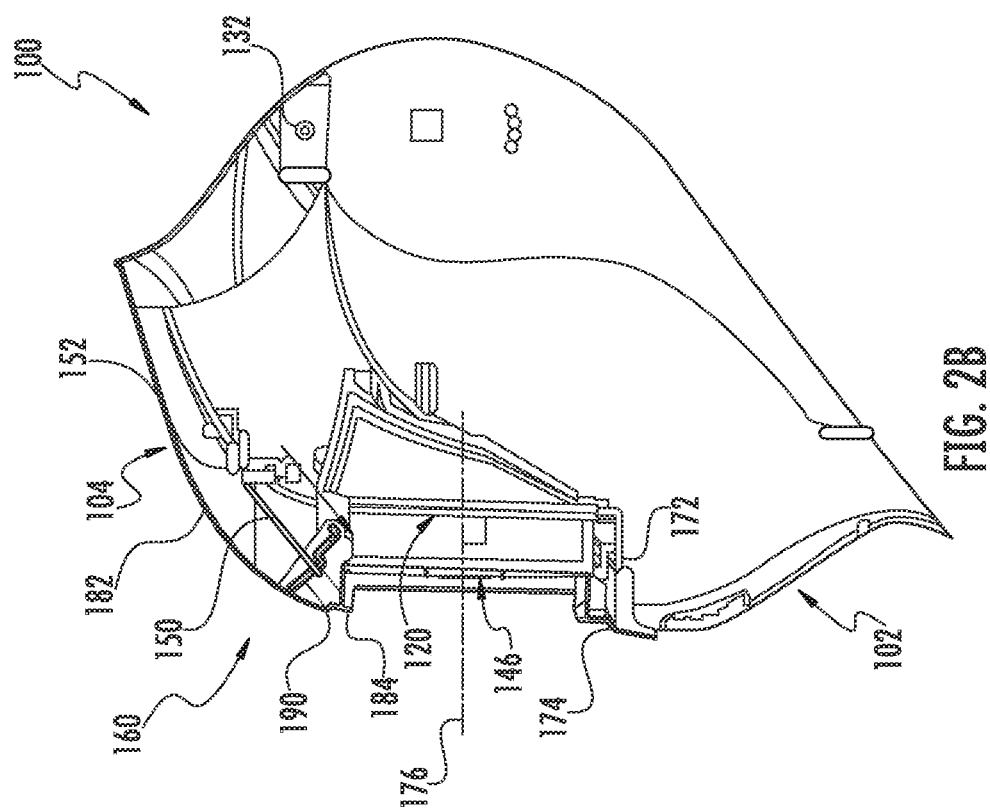
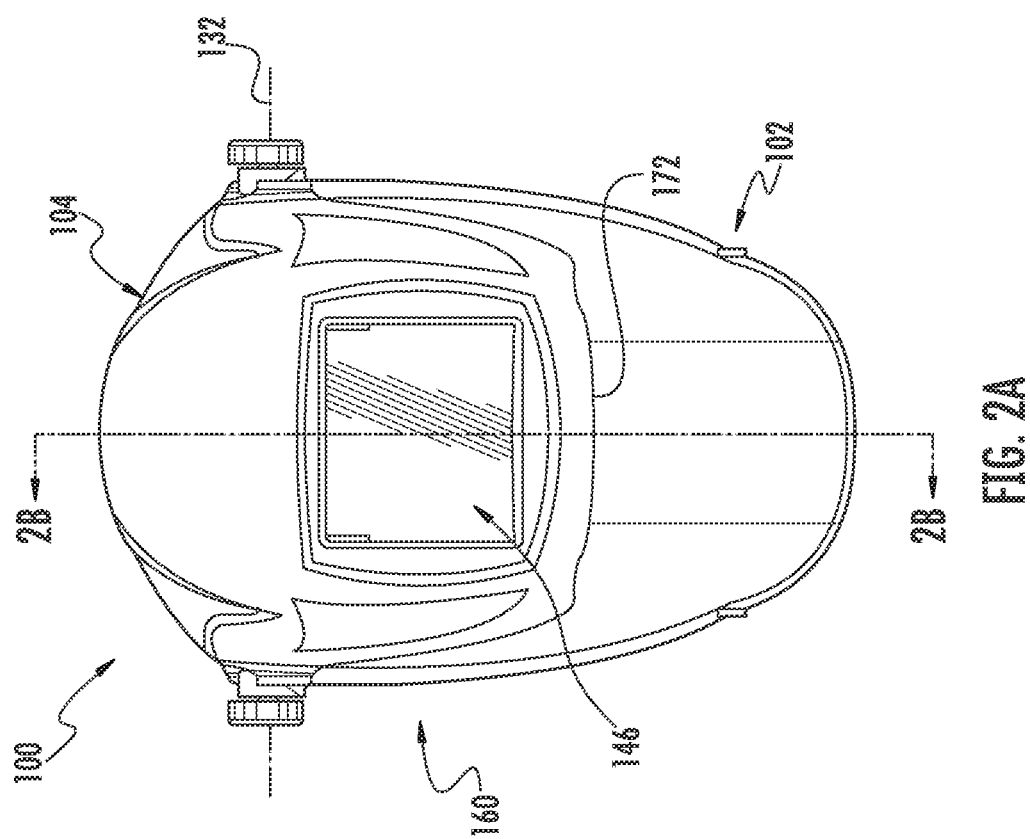

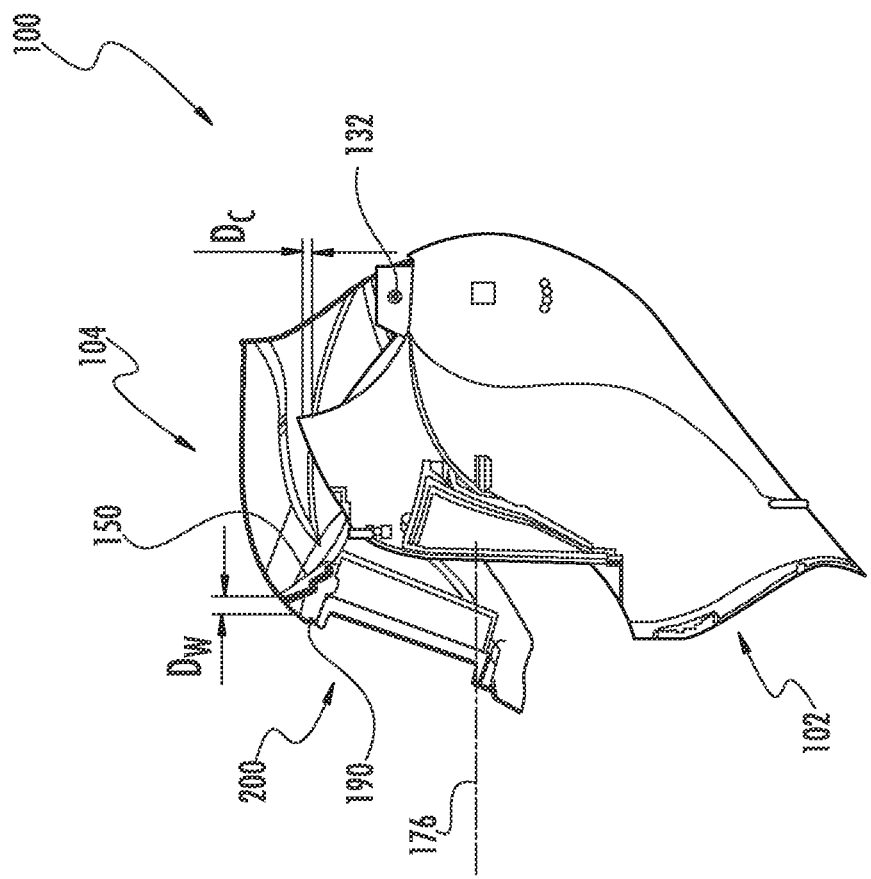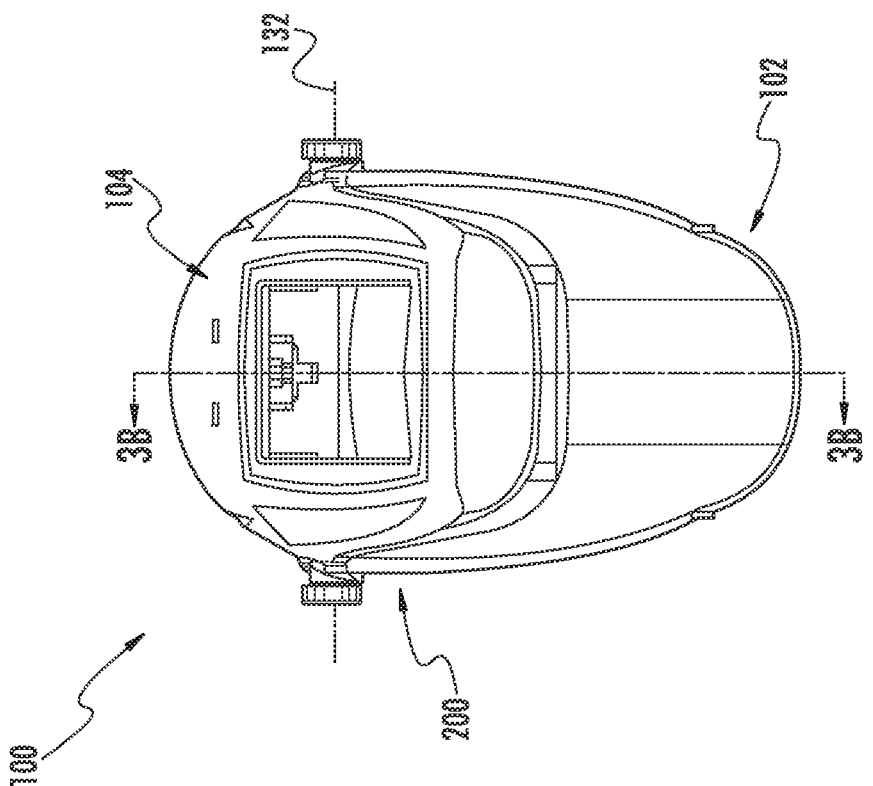

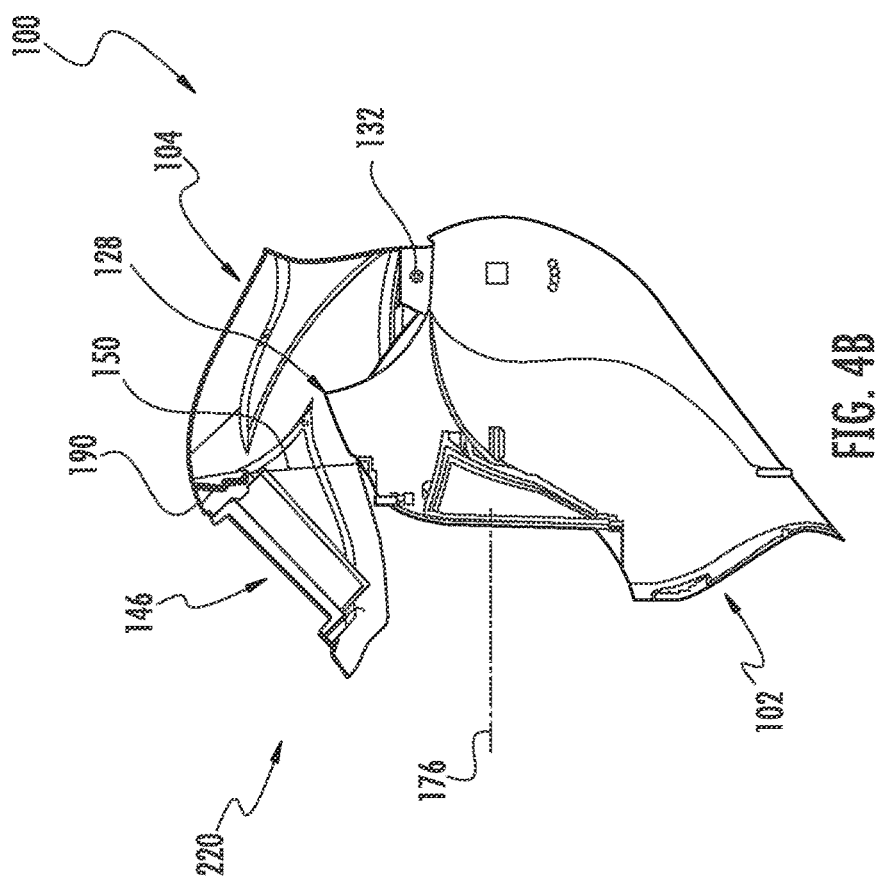
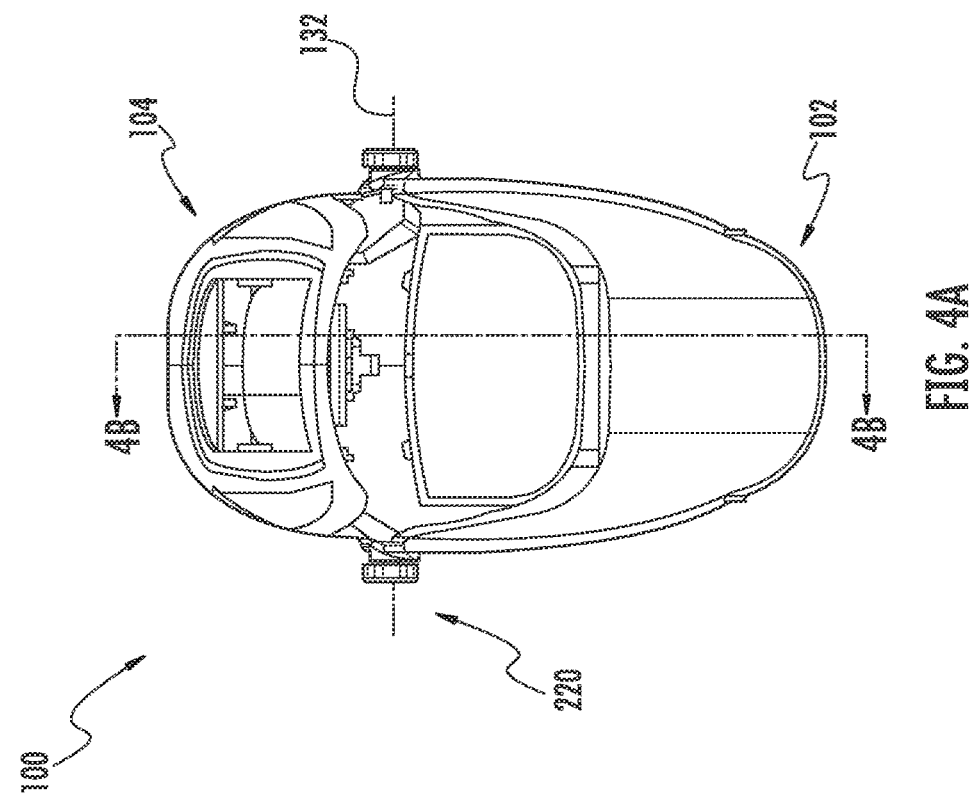

HELMET ASSEMBLIES WITH FLIP-TYPE WELDING VISORS

TECHNICAL FIELD

The present disclosure generally relates to welding helmets and, more specifically, to improvements to helmet assemblies with flip-type welding visors.

DESCRIPTION OF THE RELATED ART

Multi-purpose industrial helmets are known that provide numerous functional and safety features to a wearer. One such helmet is a flip-type helmet that incorporates head gear for mounting the helmet to the wearer and a movable welding visor. Due to various impediments to a user's ability to easily "flip" the visor, there are ongoing to improve such flip-type helmets.

SUMMARY

Improvements to helmet assemblies with flip-type welding visors are provided. In one embodiment, a return mechanism applies a predetermined force to a wireform spring. The return mechanism applies a force between a welding visor and a grinding shell, while concurrently reducing rotational forces needed to flip up the welding visor from the grinding shell. In another embodiment, a combination of an adjustable spring and a slide stop provides an adjustable stopping position for the wireform spring. The adjustable stopping position permits adjustable balancing of the forces that are applied to the wireform spring.

Other systems, methods, features, and/or advantages of the present disclosure will be or may become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 2A is a front schematic view of an example embodiment of a helmet assembly, with the welding visor in the lower position.

FIG. 2B is a cross-sectional view of the embodiment of FIG. 2A as viewed along section line 2B-2B.

FIG. 3A is a front schematic view of the embodiment of FIGS. 2A and 2B, with the welding visor in the intermediate position.

FIG. 3B is a cross-sectional view of the embodiment of FIG. 3A as viewed along section line 3B-3B.

FIG. 4A is a front schematic view of the embodiment of FIGS. 2A-3B, with the welding visor in the upper position.

FIG. 4B is a cross-sectional view of the embodiment of FIG. 4A as viewed along section line 4B-4B.

DETAILED DESCRIPTION

Figure 1:
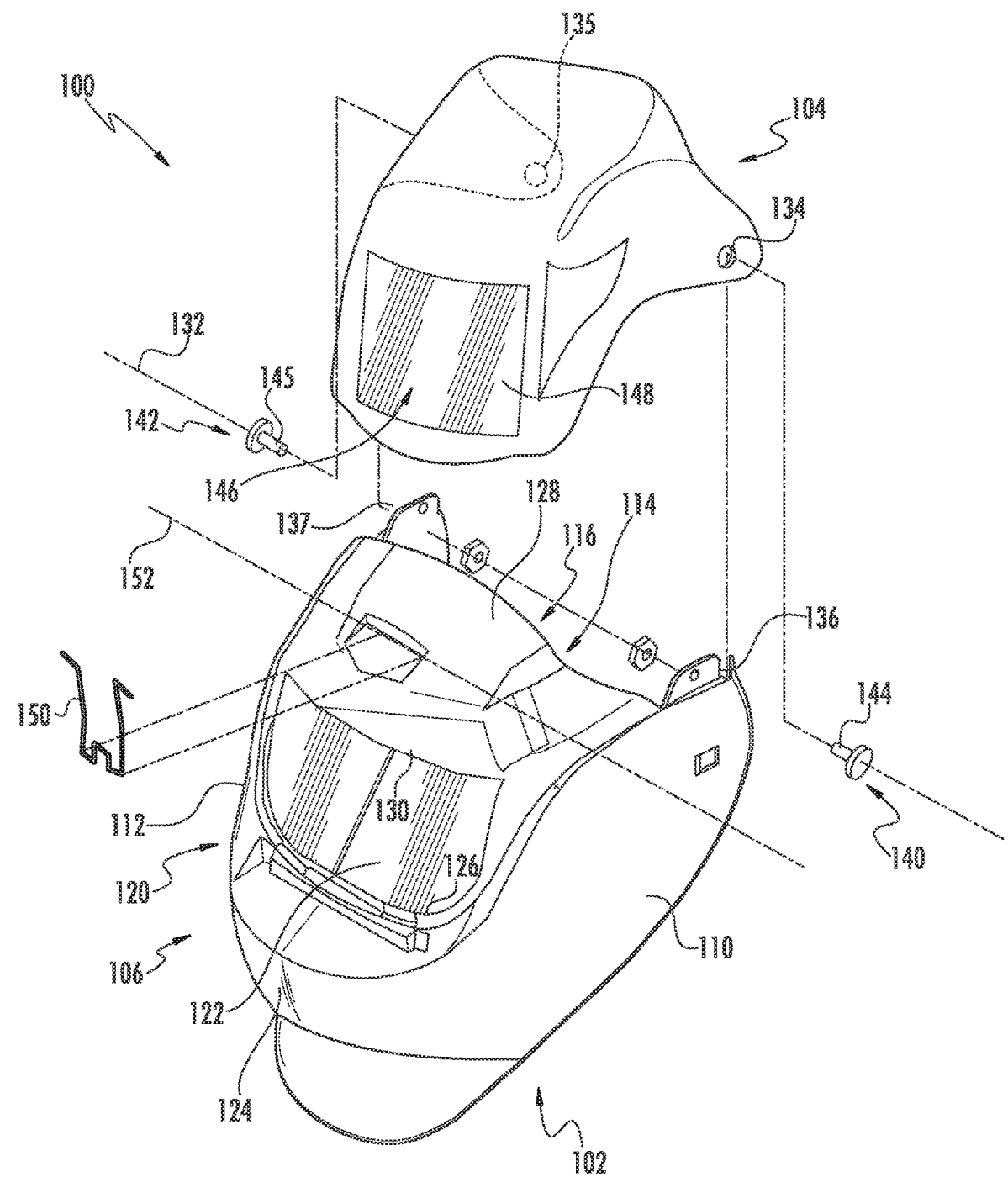
FIG. 1 is a schematic, exploded view of an example embodiment of a helmet assembly.

Having summarized various aspects of the present disclosure, reference will now be made in detail to that which is illustrated in the drawings. While the disclosure will be described in connection with these drawings, there is no intent to limit the scope of legal protection to the embodiment or embodiments disclosed herein. Rather, the intent is to cover all alternatives, modifications and equivalents included within the spirit and scope of the disclosure as defined by the appended claims.

In this regard, FIG. 1 is a schematic, exploded view of an example embodiment of a helmet assembly. As shown in FIG. 1, helmet assembly 100 includes a grinding shell 102 and a welding visor 104. The grinding shell 102 is configured to receive the head of a wearer, with mounting of the assembly to the wearer's head typically being accomplished by head gear (e.g., straps and/or bands) that is not shown in these figures. The grinding shell 102 has a front 106 for positioning near the face of a wearer, a left side 110 for positioning near the left cheek of the wearer, a right side 112 for positioning near the right cheek of the wearer, and a back 114. An opening 116 is located at the back 114 and is configured to receive the head of the wearer of the helmet assembly.

A grinding view port 120 is located at the front 106 that mounts a grinding cover plate 122 through which a wearer's line of sight is directed during a grinding operation, for example. Grinding view port 120 is defined, at least in part, by a chin portion 124 that spans between the left and right sides 110, 112 along a lower edge 126, and by a cranium portion 128 that spans between the left and right sides 110, 112 along an upper edge 130.

Welding visor 104 is mounted to grinding shell 102 and is rotatable about a rotational axis 132. In the embodiment depicted in FIG. 1, mounting of welding visor 104 to grinding shell 102 is facilitated by corresponding pairs of mounting apertures 134, 135 of welding visor 104 that align with apertures 136, 137 of grinding shell 102. Knob assemblies 140, 142 include shafts 144, 145 that extend through the apertures for retaining alignment of the apertures. In some embodiments, knob assemblies 140, 142 may enhance retention of welding visor 104 at selected positions about axis 132 by providing user-adjustable frictional engagement between welding visor 104 and grinding shell 102 such as by via an interposed rubber bushing (not shown).

Welding visor 104 incorporates a welding view port 146 that mounts a welding cover plate 148 through which a wearer's line of sight extends during a welding operation, for example. As will be described in greater detail, welding visor 104 is rotatable about rotational axis 132 between a lower position (depicted in FIG. 2A) and an upper position (depicted in FIG. 4A). In the lower position, welding visor 104 is seated against grinding shell 102 to prevent unwanted light leakage between the components. Additionally, welding view port 146 is aligned with grinding view port 120 so that a line of sight of the wearer of helmet assembly 100 extends through the grinding view port and then the welding view port. In the upper position, welding visor 104 is rotated toward the back 148 of the grinding shell so that the line of sight of the wearer is unobstructed by the welding visor. For instance, in this embodiment, the welding view port 146 is positioned above the cranium portion 128. It should be noted that the "line of sight" is a sight line extending through the grinding cover plate 122.

Also depicted in FIG. 1 is a connector 150 that extends between grinding shell 102 and welding visor 104. In this embodiment, connector 150 is a wireform that is rotatable about axis 152, which is parallel to but displaced from axis 132. Functionality of the connector will be described in detail later.

In operation, interaction of grinding shell 102 and welding visor 104 provides a biasing force to urge the welding visor towards a selected position (e.g., the lower position or the upper position). For instance, as the welding visor approaches the lower position, a biasing force is present that urges the welding visor downwardly against the grinding shell. The extent of the biasing force is derived from numerous factors, such as (but not limited to): contact surface shapes of the exterior of grinding shell 102 and the interior of welding visor 104; size and/or shape of the connector 150; location of the rotational axes (132, 152); attachment locations of the connector; and resilience of the materials forming grinding shell 102, welding visor 104 and connector 150. Preferably, the biasing force exhibited at the lower and upper positions is greater (e.g., minimally greater) than the weight of the welding visor (and any components installed thereon) in order to retain the desired position regardless of the orientation of the helmet assembly.

FIGS. 2A and 2B depict helmet assembly 100 with welding visor 102 in the lower position 160. As may be see more clearly in FIG. 2B, the lower position 160 is exhibited by lower edge 172 of welding visor 104 abutting ledge 174 of grinding shell 102 after the welding visor is rotated downwardly towards the grinding shell about axis 132. Welding visor 104 is retained in this position by a biasing force. In the lower position, line of sight 176 of a wearer of the helmet assembly extends through grinding view port 120 and welding view port 146. Preferably, welding view port 146 is aligned (to the extent possible) with grinding view port 120.

Connector 150, which extends between the exterior of grinding shell 102 and the interior of welding visor 104, includes a shell end 182 and a visor end 184. Shell end 182 is rotatably connected to grinding shell 102 so that the connector may rotate about axis 152. Visor end 184 of the connector engages welding visor 104 and assists in guiding the welding visor between the various positions relative to the grinding shell and/or to enhance the extent of biasing force applied to the welding visor. In this embodiment, engagement of connector 150 with welding visor 104 is facilitated by a pair of cam slots, only one of which (i.e., cam slot 190) is depicted in FIG. 2B. Specifically, visor end 184 of the connector engages and is guided by cam slot 190.

FIGS. 3A and 3B depict the helmet assembly 100 with welding visor 104 in an intermediate position 200. As shown in FIG. 3B, the intermediate position 200 is exhibited by lower edge 172 of welding visor 104 at least partially obstructing the line of sight 176. Notably, welding visor 104 has been rotated upwardly and rearwardly toward the back 114 of the grinding shell about axis 132.

At intermediate position 200, the biasing force exerted upon welding visor 104 reaches a maximum as potential energy is loaded into various components of the helmet assembly. In this embodiment, deflection in the material of cranium portion 128 and connector 150 are evident (shown by arrows DC for the cranium portion and DW for the connector). Note that connector 150 is depicted for clarity at its non-deformed length (which does not actually occur in this embodiment), with arrows DW representing the difference in radial path of connector visor end 184 and the welding visor 104, which is later described more fully with respect to FIG. 9.

FIGS. 4A and 4B depict helmet assembly 100 with welding visor 104 in the upper position 220. As shown in FIG. 4B, the intermediate position 220 is exhibited by the line of sight 176 of the wearer being unobstructed by the welding visor 104. Notably, welding visor 104 has been rotated upwardly and rearwardly from the intermediate position toward the back 114 of the grinding shell about axis 132.

Figure 5:
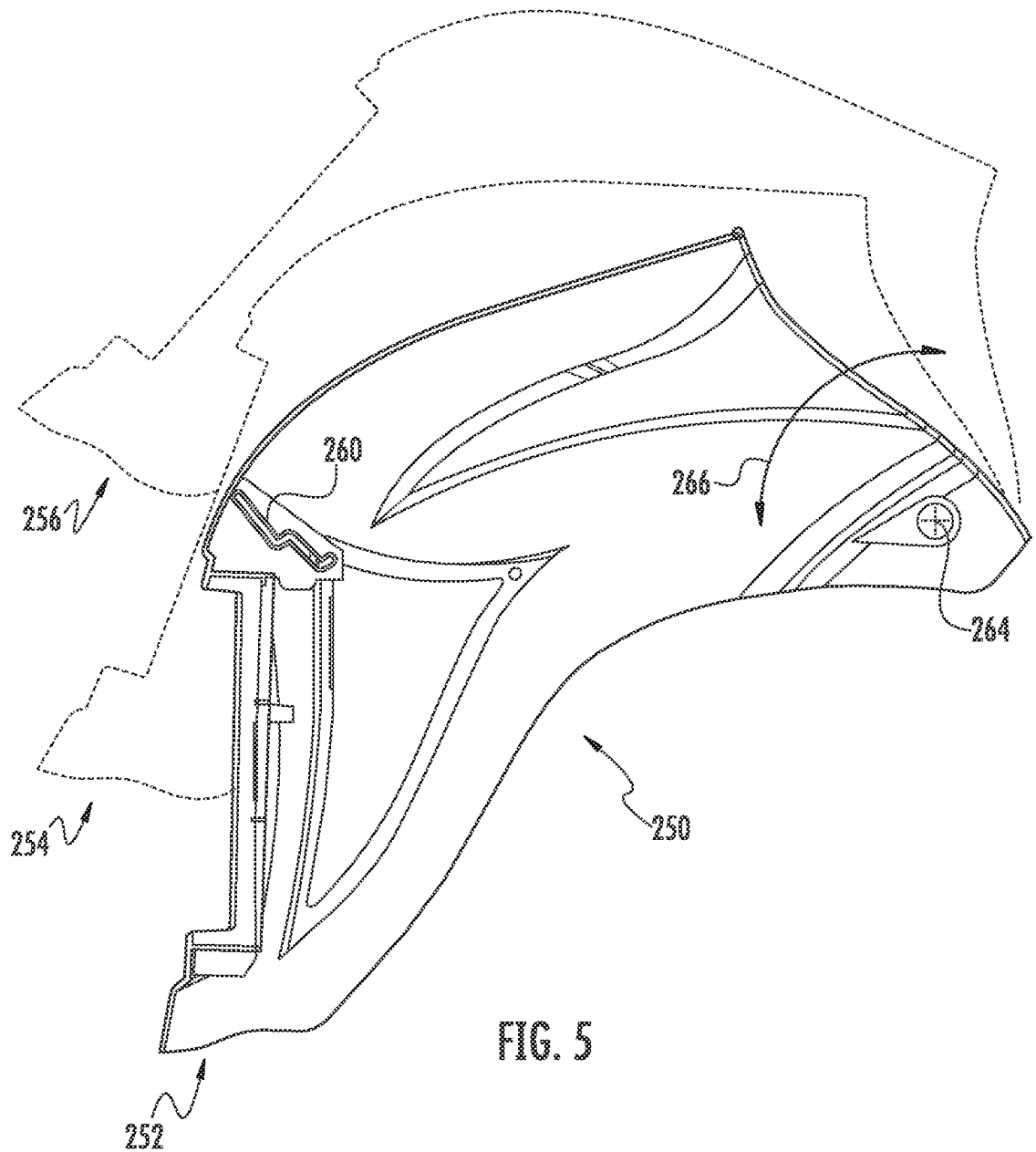
FIG. 5 is a schematic view of an example embodiment of a welding visor being rotated from the lower position, through the intermediate position, to the upper position, with the intermediate and upper positions being depicted in phantom lines.
Figure 6:
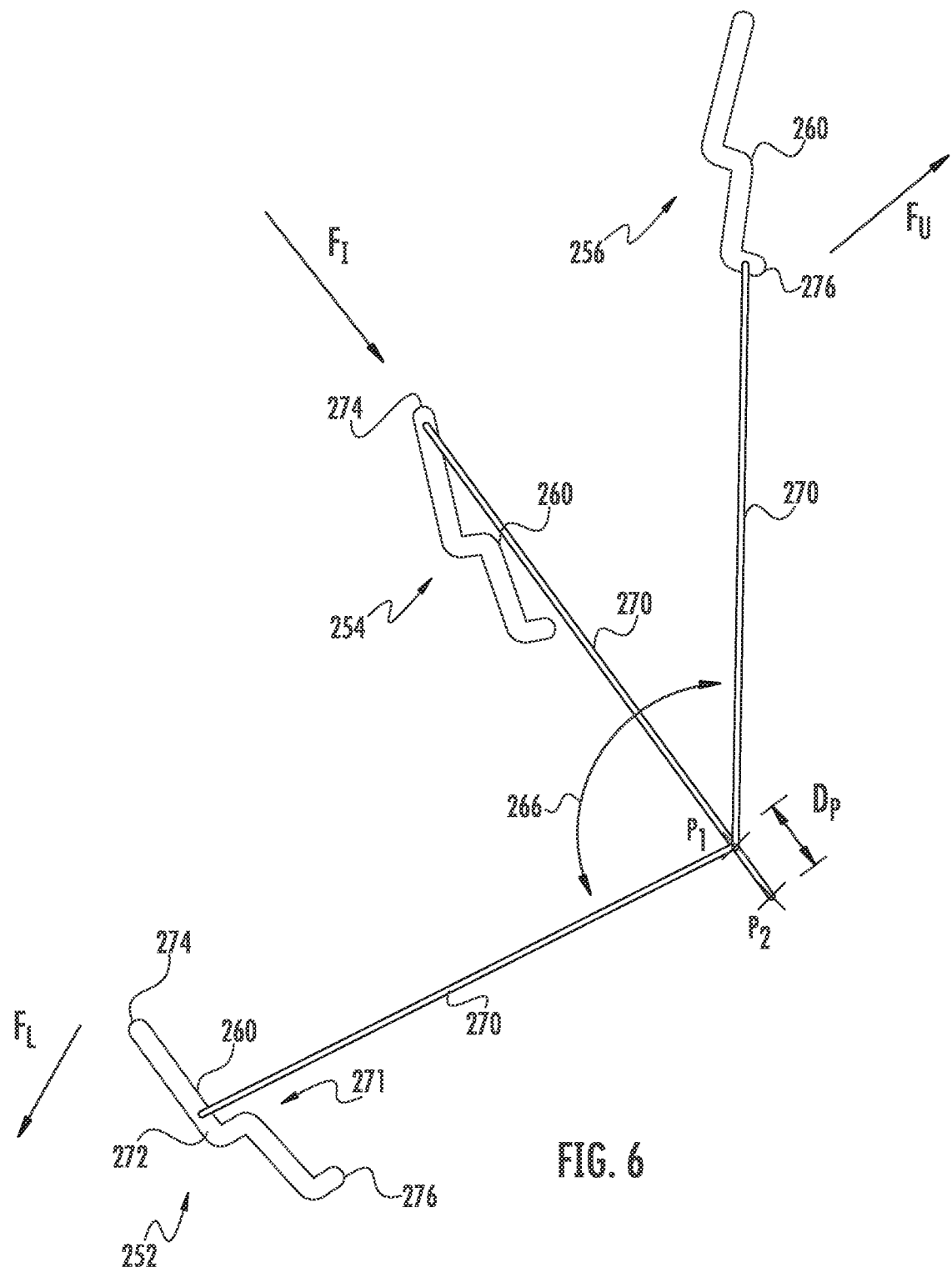
FIG. 6 is a schematic view of an example embodiment of a cam slot of the welding visor of FIG. 5 showing interaction of the cam slot and the connector.

FIGS. 5 and 6 depict a welding visor 250 being rotated from its lower position 252, through an intermediate position 254, to an upper position 256. In FIG. 5, the intermediate position 254 and upper position 256 of the welding visor are presented in phantom lines. Relative orientations of a representative cam slot 260, which is carried by an interior surface of the welding visor, are depicted with each location of the cam slot in FIG. 6 corresponding to a position of the welding visor shown in FIG. 5.

As shown in FIG. 5, repositioning of welding visor 250 from the lower position 252 to upper position 256 involves rotating the welding visor about axis 264 so that the welding visor moves through arc 266. As shown in FIG. 6, repositioning of welding visor 250 also involves the reorientation of cam slot 260 and interaction of the cam slot with connector 270.

In particular, at lower position 252, a biasing force (represented by vector FL) is present for retaining the welding visor in the lower position. In this position, connector 270 extends from point of rotation (P1) to an intermediate portion 271 of cam slot 260. As welding visor 250 is rotated along arc 266 toward intermediate position 254, distal end 272 of connector 270 is guided outwardly along the cam slot until seating at the radially outward end 274 of the cam slot.

Further movement of the welding visor along the arc with the connector seated at end 274 of the cam slot causes loading of the helmet assembly with potential energy resulting in deflection of the connector, welding visor and/or grinding shell. Note that during this movement, the biasing force has changed in direction and magnitude (represented by vector FI). In this embodiment, the various deformations cause the repositioning of the point of rotation from P1 to P2 (the deflection of the point of rotation is expressed as DP).

From intermediate position 254, continued movement of the welding visor along the arc 266 results in an unloading at least some of the potential energy as the point of rotation repositions to P1. Further movement of the welding visor causes the distal end 272 of the connector to be guided to the radially inward end 276 of the cam slot. During this movement from position 254 to position 256, the biasing force has changed again in direction and magnitude (represented by vector FU).

Figure 7:
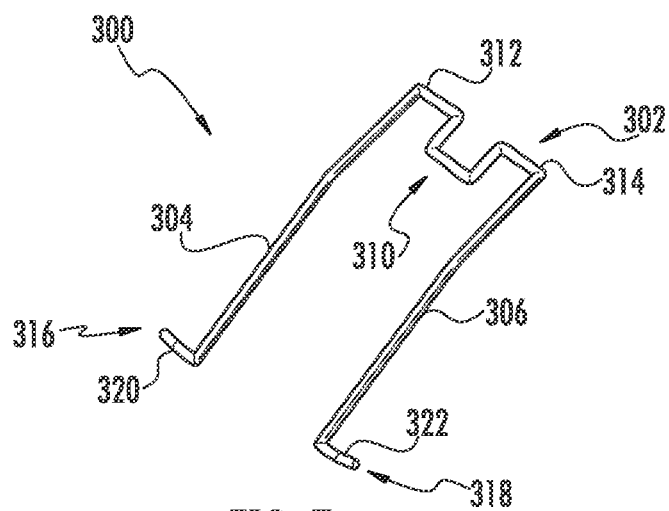
FIG. 7 is a schematic view of an example embodiment of a connector.

FIG. 7 depicts an example embodiment of a connector 300 configured as a wireform. As shown in FIG. 7, connector 300 is generally U-shaped incorporating a base 302 with arms 304, 306 extending outwardly therefrom. In this embodiment, base 302 includes an optional offset segment 310 located approximately midway between the ends 312, 314 of the base. The offset may be used to restrict side-to-side movement of the connector when implemented in conjunction with a corresponding stop positioned between the legs of the offset segment.

In the embodiment of FIG. 7, each of the arms 304, 306 exhibits an included angle of between approximately 150-170 degrees. Distal ends 316, 318 of the arms terminate in outwardly extending cams 320, 322 that are configured to engage within corresponding cam slots.

Figure 8:
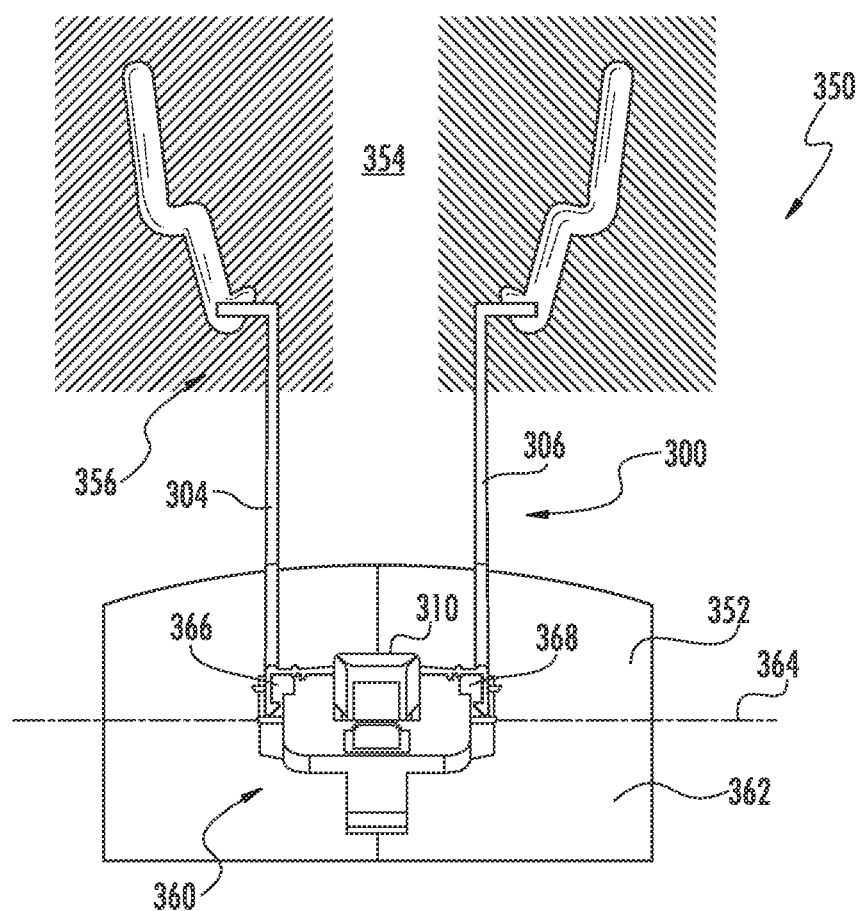
FIG. 8 is a schematic view of the connector of FIG. 7 shown retained in the upper position by an embodiment of a locking mechanism.

FIG. 8 depicts a helmet assembly 350 that includes a grinding shell 352, a welding visor 354 and connector 300 of FIG. 7. As shown in FIG. 8, the welding visor 354 is retained in the upper position 356 by an embodiment of a locking mechanism 360. Locking mechanism 360 assists in retaining welding visor 354 in the upper position by forming an interference fit with the arms 304, 306 of the connector. In particular, locking mechanism 360 is attached to cranium portion 362 of grinding shell 352 and serves as a mount for the base 302 of the connector. So attached, the connector is able to rotate about an axis 364 defined by the locking mechanism.

In one embodiment, locking lugs 366, 368 extend outwardly from locking mechanism 360. The locking lugs are positioned to capture arms 304, 306 of the connector by interference fit as the connector is carried by the welding visor during movement towards the upper position. As the arms encounter the locking lugs during this movement, continued application of force by the arms against the locking lugs deflects the arms outwardly from each other until the arms clear the locking lugs. Thus, the locking lugs form a mechanical lock of the welding visor when in the upper position that supplements the biasing force in retaining the position of the welding visor.

In another embodiment, the locking mechanism excludes locking lugs. In such an embodiment, locking of the welding visor in the upper position may be facilitated by the angles and shaped surfaces of the radially inward end 276 of the cam slot.

In order to disengage the mechanical lock, the welding visor 354 is urged toward the intermediate position with sufficient force to cause the arms to deflect away from each other for clearing the locking lugs of the locking mechanism.

Figure 9:
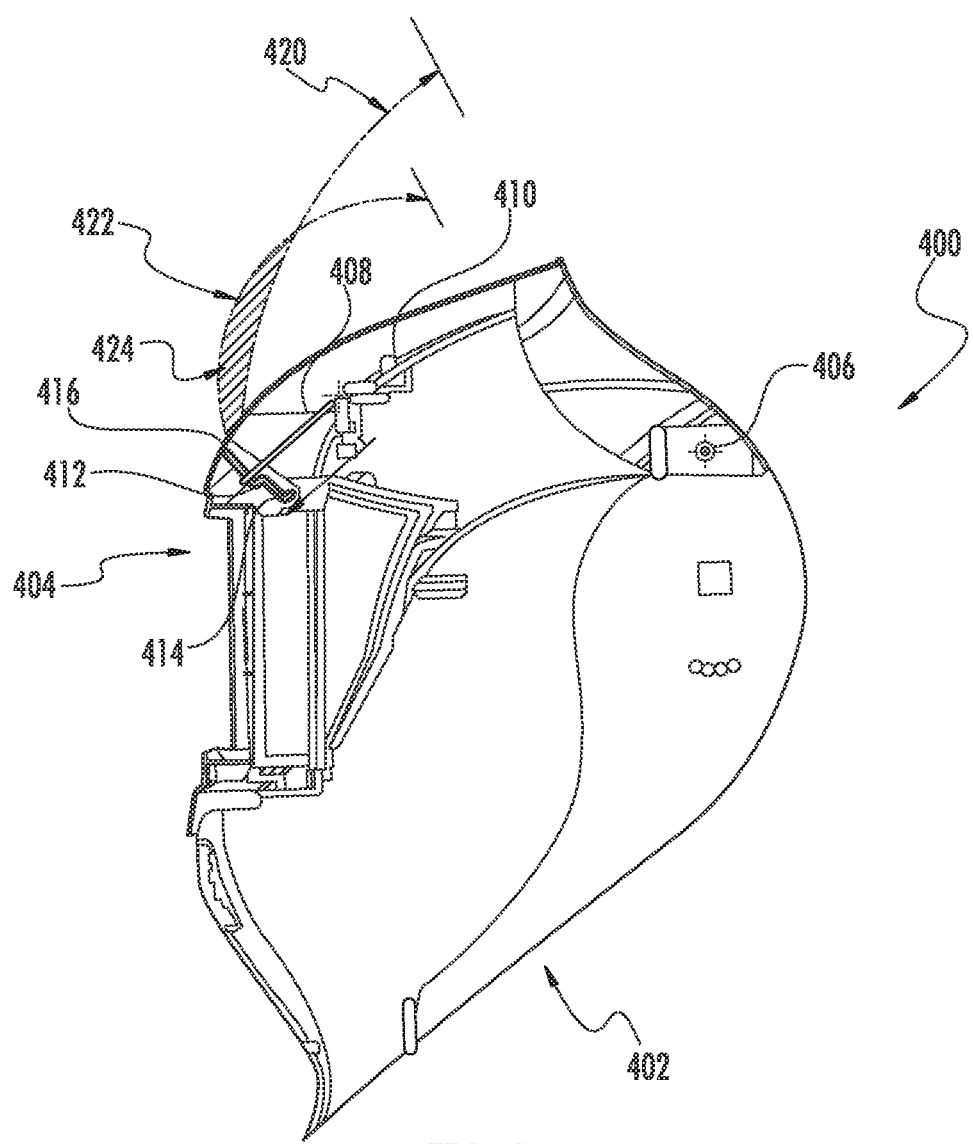
FIG. 9 is a cross-sectional view of an example embodiment of a helmet assembly.

FIG. 9 is a cross-sectional view of another embodiment of a helmet assembly 400, which includes a grinding shell 402 and a welding visor 404. Welding visor 404 is mounted to grinding shell 402 and is rotatable about a rotational axis 406. A connector 408 extends between grinding shell 402 and welding visor 404, with the connector being rotatable about axis 410. As in previous embodiments, distal ends of the connector (e.g., distal end 412 is shown in FIG. 9) ride in corresponding cam slots (e.g., slot 414).

As shown in FIG. 9, rotation of welding visor 404 about axis 406 results in the head 416 of cam slot 414 rotating along an arc 420 (depicted in dashed lines). Additionally, arc 422 (also depicted in dashed lines) represents the path along which the distal end 412 of connector 408 rotates when not being deflected during carriage by the welding visor—deflection typically occurs when connector 408 is attached to welding visor 404 resulting in biasing forces. Note that shaded region 424, which corresponds to the overlap of arcs 420 and 422, represents the locations and corresponding magnitude of biasing forces present within the helmet assembly during operation. These biasing forces are present because the distal ends of connector 408 are prevented from extending outwardly beyond the heads of the cam slot (which corresponds to arc 420) in which it rides, resulting in deflection of the connector and possibly one or more other components of the helmet assembly. These biasing forces urge the welding visor towards the selected position.

As shown in the embodiments of FIGS. 1 through 9, the connector 300 (FIG. 7), which is shown as a wireform spring 300, travels in a cam slot 260 when a user moves the welding visor 104 (FIG. 1) up or down with reference to the grinding shell 102 (FIG. 1) through a rotational motion. Multiple factors affect the force that is needed to flip the welding visor 104, these factors include flexibility (or the stiffness) of the wireform spring 300, the location of the wireform spring 300 in the cam slot 260 when the welding visor 104 is in the down position, the shape of the grinding shell 102, any modification to the upper part of the grinding shell, and/or the use of additional components within the grinding shell 102 that affect the stiffness of the grinding shell, including, though not limited to, a head harness (headgear). Thus, if any of the factors change they can significantly impact the amount of force necessary to rotate the welding visor 104 on the grinding shell 102. For example, if the wireform spring 300 is too stiff, then it becomes more difficult to flip the welding visor 104. Conversely, if the wireform spring 300 is not stiff enough, then the welding visor 104 may flip (up or down) at inconvenient moments (either due to gravity or due to movement by the user).

Another example is the harness used to hold the complete helmet to the users head. Adjusting this harness affects the shape of the grinding shell and thus its contributing factor to the force applied to resisting the rotation motion of welding visor 104 on grinding shell 102. These are but two examples of the multiple factors influencing the force applied to resisting the rotation motion of welding visor 104 on grinding shell 102.

FIGS. 10A, 10B, 10C, 11A, 11B, and 11C show embodiments that permit adjustment of a resting/stop location of the wireform spring 300 when the welding visor 104 is in the down position, thereby ameliorating issues that arise from the multiplicity of variable factors affecting the applied force on the complete spring mechanism. Specifically, FIGS. 10A, 10B, and 10C (collectively designated as FIG. 10) show an example embodiment of a return mechanism that applies a predetermined force to a wireform spring, and FIGS. 11A, 11B, and 11C (collectively designated as FIG. 11) show an example embodiment of an adjustment knob that permits an adjustable stop location of the wireform spring. Attention is now turned to these embodiments.

Figure 10A:
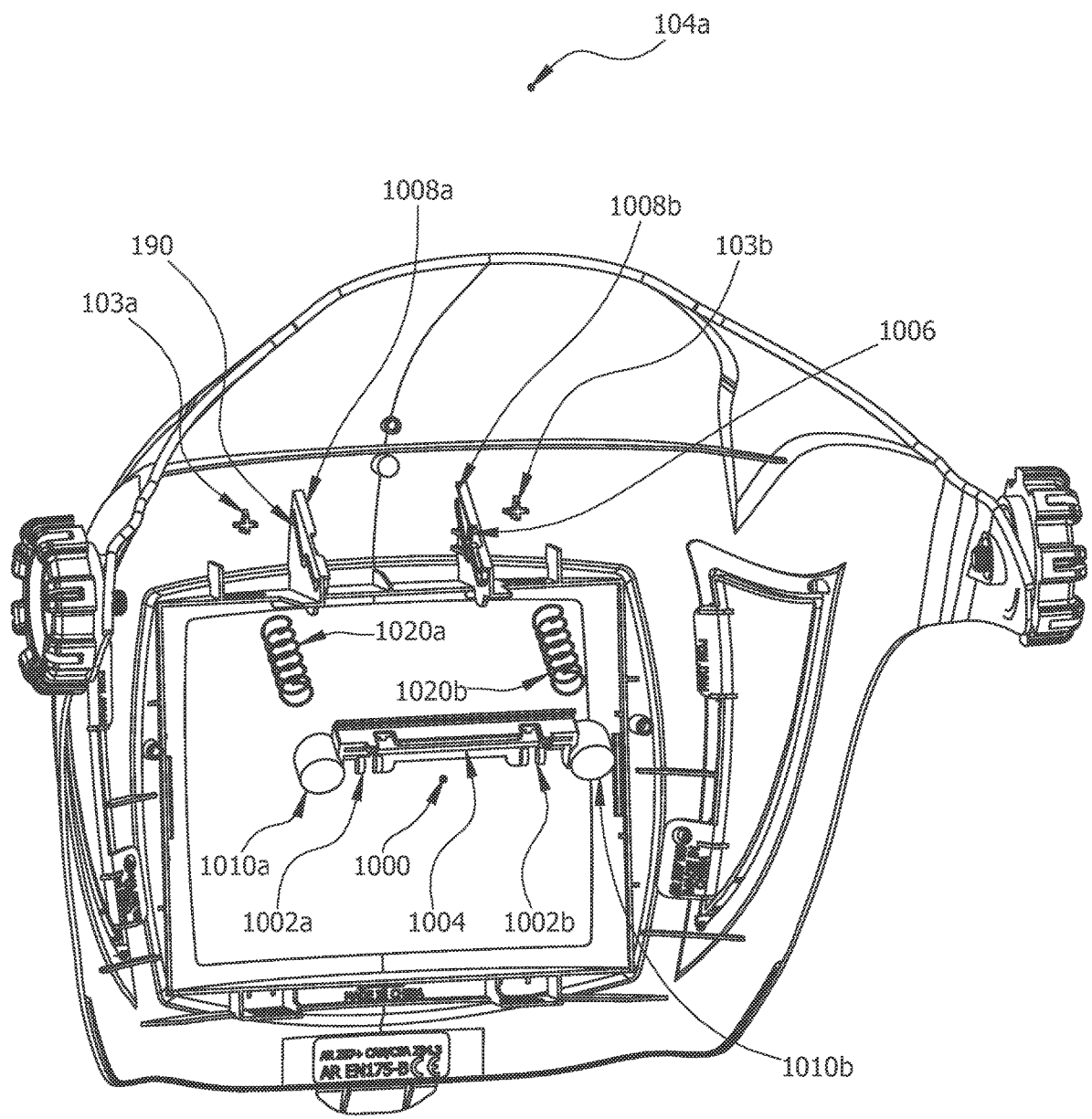
FIGS. 10A, 10B, and 10C (designated collectively as FIG. 10) are drawings showing an example embodiment of a helmet assembly with a return mechanism that applies a predetermined force to a wireform spring.
Figure 10B:
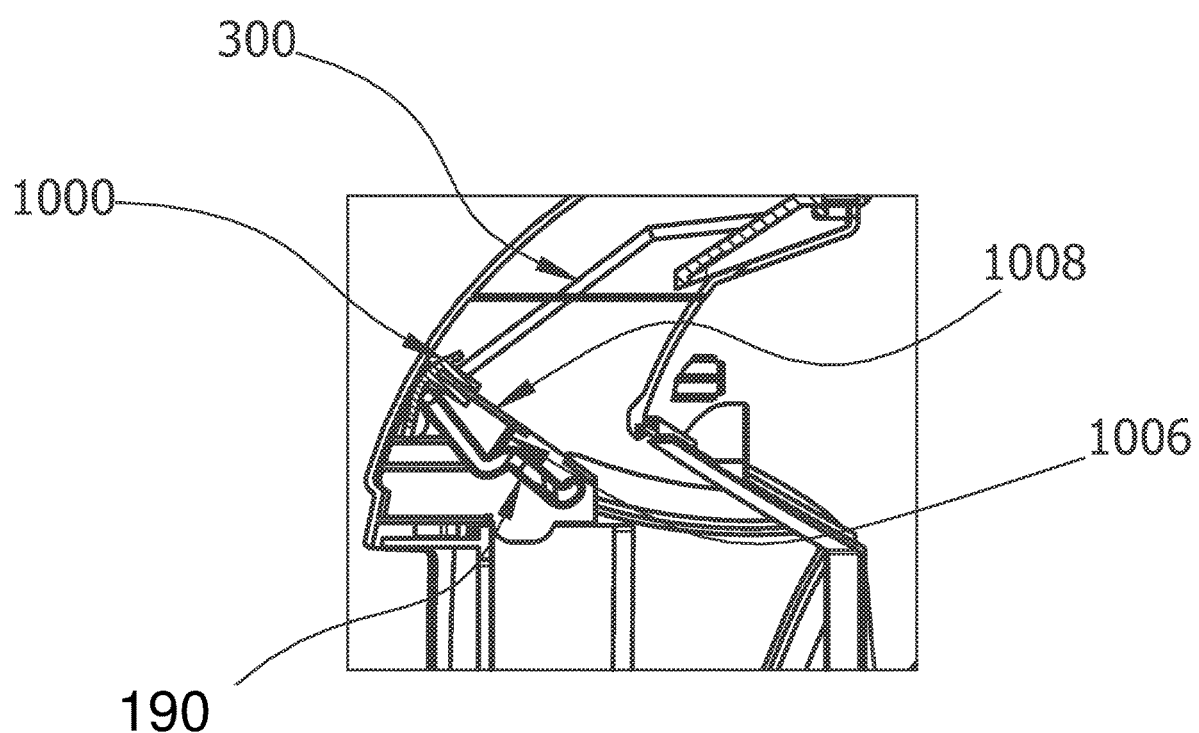
Figure 10C:
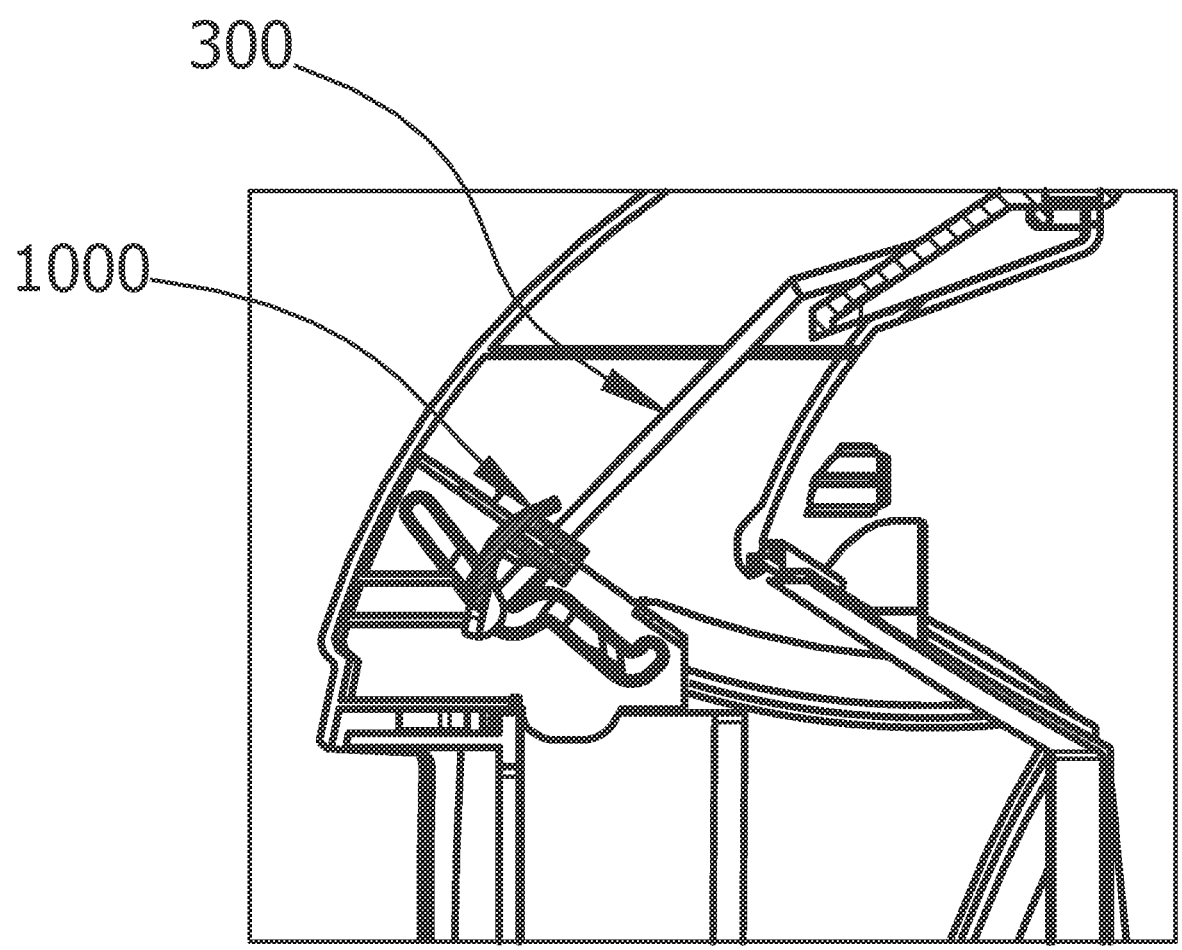

FIG. 10 shows one embodiment of a welding visor 104a, which is similar to the welding visor 104 of FIG. 1. Specifically, FIG. 10A shows a perspective view of the embodiment, while FIG. 10B shows a profile view as the welding visor 104a is moved from a lower position to a middle position, and FIG. 10C shows the same profile view as FIG. 10B but as wireform spring returns to its initial position.

Recalling, the welding visor 104 of FIG. 1 comprises a pair of cam slots 190 in which a wireform spring 300 travels, thereby permitting controlled movement of the welding visor 104 (FIG. 1) with reference to the grinding shell 102 (FIG. 1). In addition to the components of the welding helmet assembly 100 shown in FIG. 1, the welding visor 104a of FIG. 10 comprises a pair of return spring bosses 1030a, 1030b (collectively, 1030) located near the cam slots 190. Additionally, the embodiment of FIG. 10 comprises a return mechanism 1000 with a pair of cylinders 1010a, 1010b (collectively, 1010) on each side of the return mechanism 1000, and a pair of return compression springs 1020a, 1020b (collectively, 1020). One end of each return compression spring 1020 engages its respective return spring boss 1030. The other end of each return compression spring 1020 nests within its respective cylinder 1010 on the return mechanism 1000.

When mounted, the return mechanism 1000 slides along return slide rails 1008a, 1008b (collectively 1008) with lobes 1002a, 1002b (collectively 1002) of the return mechanism 1000 engaging one end of the wireform spring 300. In other words as shown in FIG. 10B, the return mechanism 1000 applies a force to the wireform spring 300 from the return compression springs 1020, thereby positioning the wireform spring 300 to an optimal, fixed position. The fixed position is based on a size of a stop bar 1004 and a fixed position of a stop rib 1006 on welding visor 104a, which apply the desired force necessary to the complete wireform spring-assisted movement. Without the return mechanism 1000, the wireform spring 300 can move, depending on the multiple factors listed above into a non-optimal position. The applied force results in a repositioning of the wireform spring 300, thereby effectively changing the amount of additional force needed to flip the welding visor 104a. Furthermore, because the return mechanism 1000 returns the wireform spring 300 to a predetermined location (and consequently resulting in a pre-compression of the wireform spring 300) when the welding visor 104a is flipped down, the return mechanism 1000 provides a balance between forces, namely, between the force needed to flip up the welding visor 104a and the force needed to prevent the welding visor 104a from inadvertently flipping up.

Figure 11A:
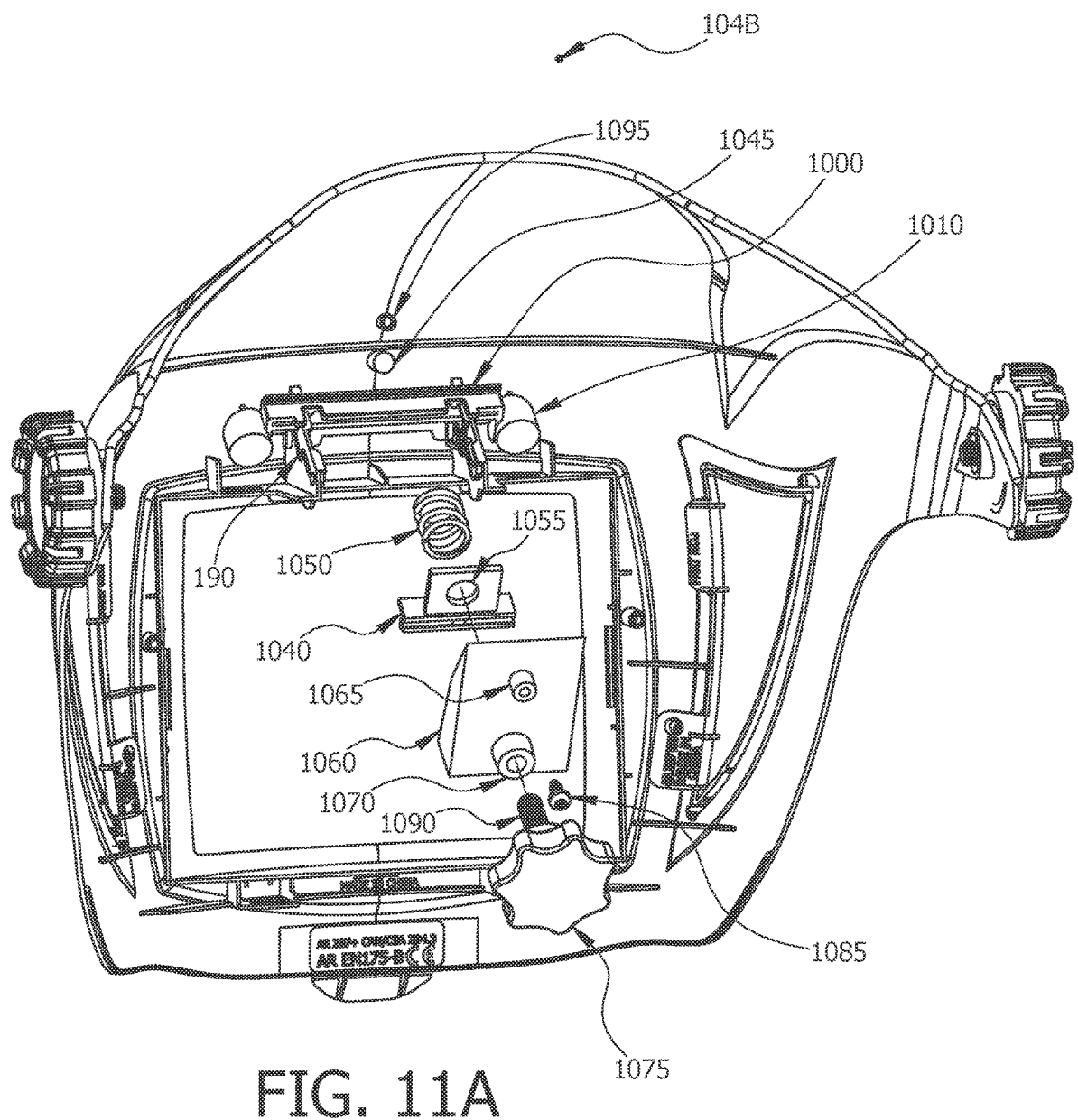
FIGS. 11A, 11B, and 11C (designated collectively as FIG. 11) are drawings showing an example embodiment of a helmet assembly with an adjustment knob that permits an adjustable location to a stop position of a wireform spring when a welding visor is in the down position.
Figure 11B:
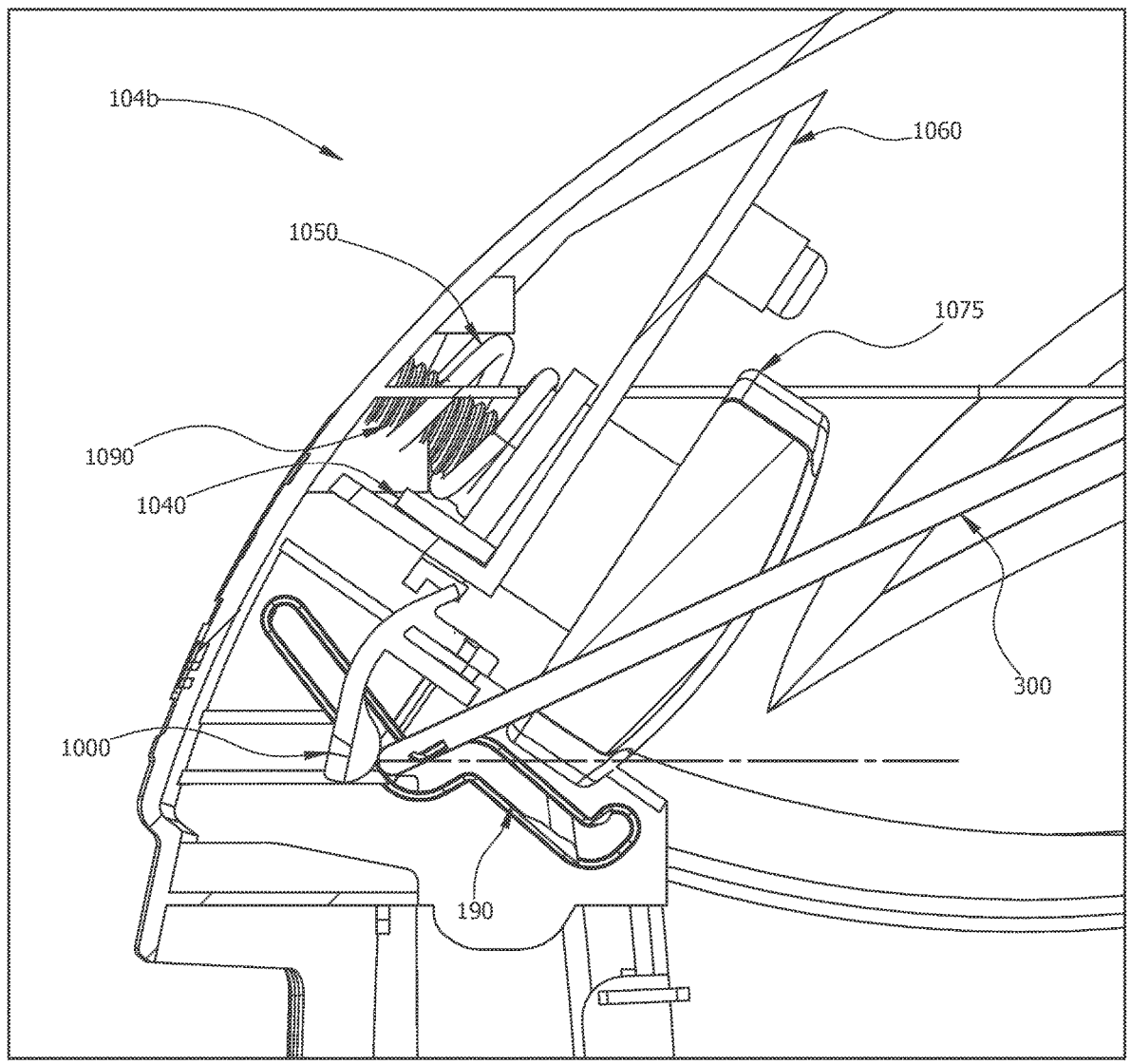
Figure 11C:
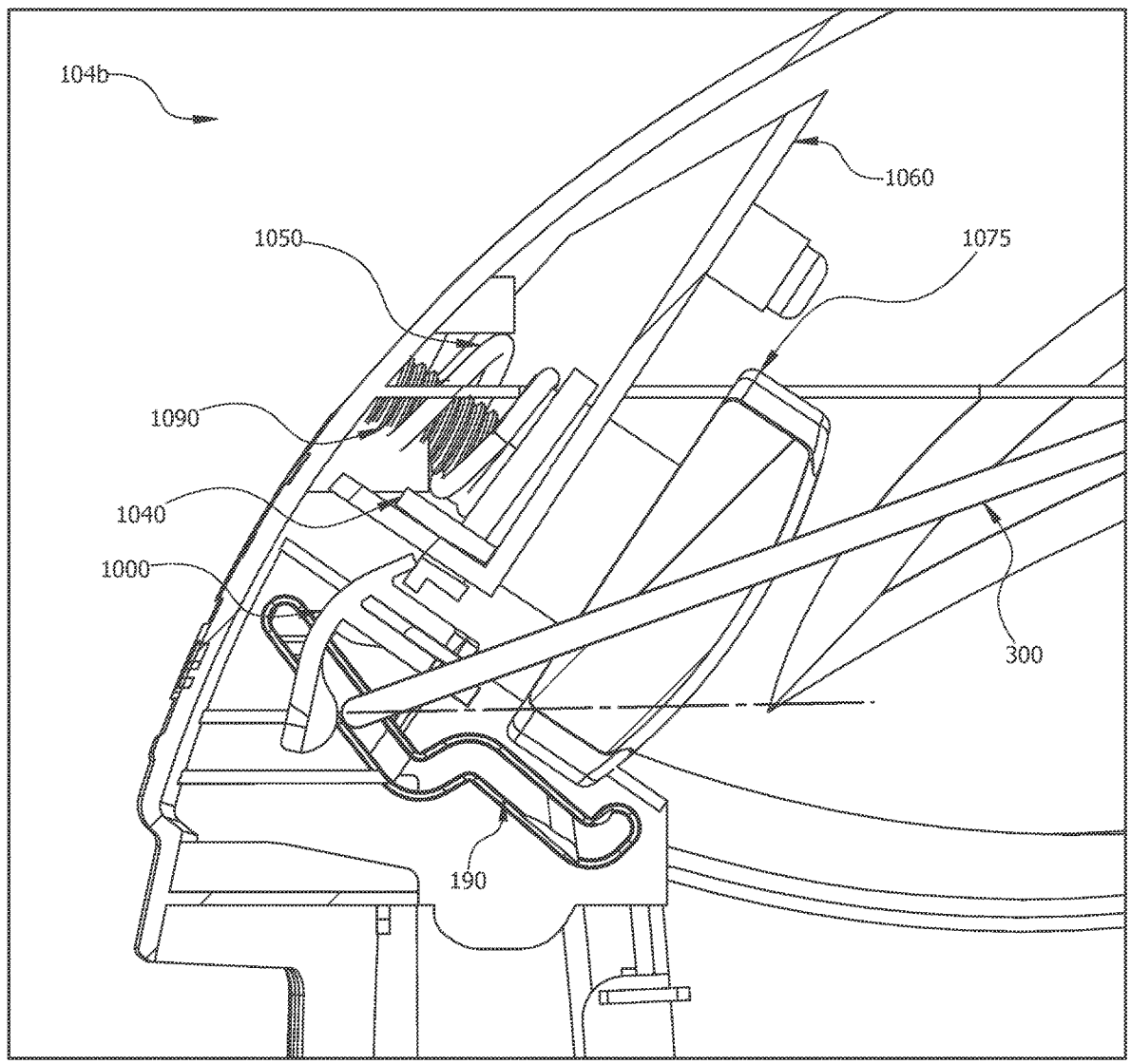

Although the embodiment of FIG. 10 provides a fixed pre-compression of the wireform spring 300, it is also possible to provide a variable compression to the wireform spring 300 by a mechanism such as that shown in FIG. 11. Specifically, FIG. 11A shows a perspective view of this embodiment, while FIGS. 11B and 11C show profile views where more force (FIG. 11B) and less force (FIG. 11C) are applied to the return mechanism 1000 by the use of an adjustment knob 1075.

The embodiment of FIG. 11 comprises the return mechanism 1000 (shown mounted to the welding visor 104b through cylinders 1010). Additionally, the embodiment of FIG. 11 comprises a slide stop 1040, an adjustable spring 1050, a spring boss 1045, a slide stop cover 1060, a screw 1085, a visor screw hole 1095, and a slide stop adjustment knob 1075 with a threaded bolt 1090.

Structurally, the slide stop 1040 comprises a threaded hole 1055, which has dimensions that can accommodate the threaded bolt 1090 of the adjustment knob 1075. The slide stop cover 1060 comprises a cover screw hole 1065 (for the screw 1085) and a bore 1070 (for the threaded bolt 1090). The adjustable spring 1050 resides between the spring boss 1045 and the slide stop 1040, with one end of the adjustable spring 1050 engaging the spring boss 1045 and the other end of the adjustable spring 1050 engaging the slide stop 1040. The slide stop cover 1060 holds the slide stop 1040 against the adjustable spring 1050, which in turn is held to the welding visor 104b by the spring boss 1045. The slide stop cover 1060 is secured to the welding visor 104b by the screw 1085, which threads both the cover screw hole 1065 and the visor screw hole 1095. The threaded bolt 1090 inserts into the bore 1075 and rotationally mates with the threaded hole 1055.

Thus, if a user turns the adjustment knob 1075 in one direction, then the slide stop 1040 compresses the adjustable spring 1050. Similarly, if the user turns the adjustment knob 1075 in the other direction, then the slide stop 1040 decompresses the adjustable spring 1050. The ability to selectively compress and decompress the adjustable spring 1050 results in controlled variability of the location of the return mechanism 1000. This ability to control the location of the return mechanism 1000 results in a corresponding ability to control the forces that are needed to flip the welding visor 104b as shown in FIGS. 11B and 11C.

Structurally, the embodiment of FIG. 10 comprises a grinding shell 102 (FIG. 1) and a welding visor 104a rotatably coupled to the grinding shell 102 (FIG. 1). The welding visor 104a has an inside and an outside. The embodiment of FIG. 10A further comprises a cam slot 190 located on the inside of the welding visor 104a, and a spring boss 1030 that is also located on the inside of the welding visor 104a. The spring boss 1030 is located beside the cam slot 190. The embodiment of FIG. 10 further comprises a compression spring 1020 having a first end and a second end, with the first end of the compression spring being mechanically coupled to the spring boss 1030. The embodiment of FIG. 10 further comprises a wireform spring 300 having a sliding end and a rotating end, with the sliding end of the wireform spring 300 being slidably engaged to the cam slot 190, and the rotating end of the wireform spring 300 being rotatably engaged to the grinding shell 102 (see FIG. 1). The embodiment of FIG. 10 further comprises a return mechanism 1000, which is mechanically coupled to the second end of the compression spring 1020. The return mechanism 1000 applies a compression force to the compression spring 1020. The return mechanism 1000 further defines a starting position from which the sliding end of the wireform spring 300 slidably engages the cam slot 190.

It should be appreciated that the pre-tensioning of the return mechanism (as shown in FIG. 10) and the adjustable mechanism (as shown in FIG. 11) are not trivial or routine improvements of the helmet assembly 100 of FIGS. 1 through 9. This is because problems relating to the stiffness of the wireform spring 300 are not readily apparent from FIGS. 1 through 9. Furthermore, because the pre-tensioning provided by the return mechanism 1000 must avoid interfering with the movement of the wireform spring 300 as the wireform spring 300 travels along the cam slots 190, designing and implementing the return mechanism 1000 requires consideration of multiple factors. Furthermore, because the adjustment mechanism (shown in FIG. 11) must not hinder or obstruct the movement of the wireform spring 300 along the cam slots 190, the adjustment mechanism (FIG. 11) requires consideration of even more factors. Stated differently, those having ordinary skill in the art will understand that the problem of a wireform spring 300 being too stiff (or not stiff enough) is not one that can be readily appreciated by mere reference to FIGS. 1 through 9, and that the particular solutions to this problem, as described in FIGS. 10 and 11, require particular considerations of the behavior of the wireform spring 300, with those considerations being neither trivial nor insignificant.

It should be emphasized that the above-described embodiments are merely examples of possible implementations. Many variations and modifications may be made to the above-described embodiments without departing from the principles of the present disclosure. All such modifications and variations are intended to be included herein within the scope of this disclosure and protected by the following claims.

What is claimed is:

1. A helmet assembly, comprising:
   a grinding shell;
   a welding visor rotatably coupled to the grinding shell, the welding visor having an inside and an outside;
   a cam slot located on the inside of the welding visor;
   a spring boss located on the inside of the welding visor, the spring boss being located beside the cam slot;
   a compression spring having a first end and a second end, the first end of the compression spring being mechanically coupled to the spring boss;
   a wireform spring having a sliding end and a rotating end, the sliding end of the wireform spring being slidably engaged to the cam slot, the rotating end of the wireform spring being rotatably engaged to the grinding shell; and
   a return mechanism mechanically coupled to the second end of the compression spring, the return mechanism applying a compression force to the compression spring, the return mechanism defining a starting position from which the sliding end of the wireform spring slidably engages the cam slot.

2. The helmet assembly of claim 1, wherein the cam slot is a first cam slot, wherein the spring boss is a first spring boss, wherein the compression spring is a first compression spring, and wherein the helmet assembly further comprises:
   a second cam slot;
   a second spring boss located on the inside of the welding visor, the second spring boss being located beside the second cam slot; and
   a second compression spring having a first end and a second end, the first end of the second compression spring being mechanically coupled to the second spring boss.

3. The helmet assembly of claim 2, the return mechanism comprising:
   a left cylinder configured to nest the second end of the first compression spring within the left cylinder; and
   a right cylinder configured to nest the second end of the second compression spring within the right cylinder.

4. The helmet assembly of claim 2, wherein the return mechanism resides atop the first cam slot and the second cam slot.

5. The helmet assembly of claim 1, the return mechanism comprising a cylinder configured to nest the second end of the compression spring within the cylinder.

6. The helmet assembly of claim 1, wherein the return mechanism resides atop the cam slot.

7. The helmet assembly of claim 1, further comprising:
   an adjustable spring having a first end and a second end, the first end of the adjustable spring being mechanically coupled to the return mechanism;
   a slide stop having a threaded bore, the slide stop being mechanically coupled to the second end of the adjustable spring, the adjustable spring being compressed between the slide stop and the return mechanism;
   a cover positioned over the slides top and the adjustable spring, the cover being secured to the welding visor, the cover comprising a cover bore; and
   an adjustment knob having a threaded bolt, the threaded bolt being positioned through the cover bore, the threaded bolt being rotationally coupled to the threaded bore of the slide stop.

8. The helmet assembly of claim 7, wherein turning the adjustment knob in one rotational direction compresses the adjustable spring, wherein turning the adjustment knob in another rotational direction decompresses the adjustable spring.

9. The helmet assembly of claim 7, further comprising:
   a screw for securing the cover to the welding visor.

10. A helmet assembly, comprising:
    a grinding shell;
    a welding visor rotatably coupled to the grinding shell, the welding visor having an inside and an outside;
    a cam slot located on the inside of the welding visor;
    a spring boss located on the inside of the welding visor, the spring boss being located beside the cam slot;
    a compression spring having a first end and a second end, the first end of the compression spring being mechanically coupled to the spring boss;
    a wireform spring having a sliding end and a rotating end, the sliding end of the wireform spring being slidably engaged to the cam slot, the rotating end of the wireform spring being rotatably engaged to the grinding shell;
    a return mechanism mechanically coupled to the second end of the compression spring, the return mechanism applying a compression force to the compression spring, the return mechanism defining a starting position from which the sliding end of the wireform spring slidably engages the cam slot;
    an adjustable spring having a first end and a second end, the first end of the adjustable spring being mechanically coupled to the return mechanism;
    a slide stop having a threaded bore, the slide stop being mechanically coupled to the second end of the adjustable spring, the adjustable spring being compressed between the slide stop and the return mechanism;
    a cover positioned over the slides top and the adjustable spring, the cover being secured to the welding visor, the cover comprising a cover bore; and
    an adjustment knob having a threaded bolt, the threaded bolt being positioned through the cover bore and rotationally coupling with the threaded bore of the slide stop.

11. The helmet assembly of claim 10, wherein turning the adjustment knob in one rotational direction compresses the adjustable spring, wherein turning the adjustment knob in another rotational direction decompresses the adjustable spring.

12. The helmet assembly of claim 10, further comprising a screw for securing the cover to the welding visor.

* * * * *